(12) United States Patent
Walker

(10) Patent No.: US 8,292,964 B2
(45) Date of Patent: Oct. 23, 2012

(54) SURFACE GUIDED KNEE REPLACEMENT

(75) Inventor: Peter Stanley Walker, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 11/542,904

(22) Filed: Oct. 4, 2006

(65) Prior Publication Data

US 2007/0135925 A1     Jun. 14, 2007

Related U.S. Application Data

(63) Continuation-in-part of application No. 11/304,107, filed on Dec. 14, 2005.

(51) Int. Cl.
*A61F 2/38*     (2006.01)
(52) U.S. Cl. ................... 623/20.21; 623/20.19
(58) Field of Classification Search .............. 623/20.21, 623/20.14, 20.15, 20.26–20.31; *A61F 2/38*
See application file for complete search history.

(56) References Cited

U.S. PATENT DOCUMENTS

| | | | |
|---|---|---|---|
| 5,330,533 A | 7/1994 | Walker | |
| 5,702,460 A | 12/1997 | Carls et al. | |
| 5,702,466 A | 12/1997 | Pappas et al. | |
| 6,039,764 A | 3/2000 | Pottenger et al. | |
| 6,074,425 A | 6/2000 | Pappas | |
| 6,117,175 A | 9/2000 | Bosredon | |
| 6,123,729 A | 9/2000 | Insall et al. | |
| 6,126,693 A | 10/2000 | O'Neil et al. | |
| 6,152,960 A | 11/2000 | Pappas | |
| 6,165,222 A | 12/2000 | Hoeppner et al. | |
| 6,203,576 B1 | 3/2001 | Afriat et al. | |
| 6,206,926 B1 | 3/2001 | Pappas | |
| 6,217,619 B1 | 4/2001 | Keller | |
| 6,235,060 B1 * | 5/2001 | Kubein-Meesenburg et al. | 623/20.31 |
| 6,299,645 B1 * | 10/2001 | Ogden | 623/20.21 |
| 6,325,828 B1 * | 12/2001 | Dennis et al. | 623/20.14 |
| 6,406,497 B2 * | 6/2002 | Takei | 623/20.31 |

(Continued)

OTHER PUBLICATIONS

Raymond P. Robinson, "The Early Innovators of Today's Resurfacing Condylar Knees", Arthroplasty, vol. 20, Suppl 1, 2005.

*Primary Examiner* — Thomas J Sweet
*Assistant Examiner* — Jason-Dennis Stewart
(74) *Attorney, Agent, or Firm* — Kelley Drye & Warren LLP

(57) ABSTRACT

An artificial knee joint that includes a femoral component with a specially shaped bearing surface and a tibial component, whose surface interacts with the femoral surfaces. The interaction provides for the motion and stability characteristics of the anatomic knee. The interaction between the femoral and tibial surfaces is such that as the knee is flexed to maximum, the femoral component moves posteriorly on the tibial surface, more so on the lateral side than on the medial side. This is accomplished by the interaction of a projecting tibial post inside a cupola in the center of the femoral component, and by the saggital radius on the medial side being smaller than that on the lateral side. The prevention of anterior sliding of the femur on the tibia in early flexion is accomplished by the interaction between a distal-anterior recess on the medial side of the femur and an apposing raised pad on the tibial surface. Rotational laxity at all angles is allowed by the presence of only one recess pad and by non-conforming femoral-tibial surfaces on the lateral side.

13 Claims, 4 Drawing Sheets

U.S. PATENT DOCUMENTS

| | | | |
|---|---|---|---|
| 6,416,552 B1 | 7/2002 | Hoeppner et al. | |
| 6,443,991 B1 | 9/2002 | Running | |
| 6,527,807 B1 | 3/2003 | O'Neil et al. | |
| 6,540,786 B2 | 4/2003 | Chibrac et al. | |
| 6,589,283 B1 * | 7/2003 | Metzger et al. | 623/20.35 |
| 6,616,696 B1 | 9/2003 | Merchant | |
| 6,770,097 B2 | 8/2004 | Leclercq | |
| 6,846,329 B2 * | 1/2005 | McMinn | 623/20.14 |
| 6,887,276 B2 | 5/2005 | Gerbec et al. | |
| 6,893,467 B1 | 5/2005 | Bercovy | |
| 6,902,582 B2 * | 6/2005 | Kubein-Meesenburg et al. | 623/20.31 |
| 6,962,607 B2 | 11/2005 | Gundlapalli et al. | |
| 6,986,791 B1 | 1/2006 | Metzger | |
| 7,025,788 B2 | 4/2006 | Metzger et al. | |
| 7,264,635 B2 * | 9/2007 | Suguro et al. | 623/20.14 |
| 7,326,252 B2 | 2/2008 | Otto et al. | |
| 7,354,454 B2 | 4/2008 | Stack et al. | |
| 7,364,590 B2 | 4/2008 | Siebel | |
| 7,413,577 B1 * | 8/2008 | Servidio | 623/20.14 |
| 7,497,874 B1 | 3/2009 | Metzger et al. | |
| 2002/0010512 A1 * | 1/2002 | Takei | 623/20.31 |
| 2002/0022889 A1 | 2/2002 | Chibrac et al. | |
| 2002/0120340 A1 | 8/2002 | Metzger et al. | |
| 2004/0143339 A1 * | 7/2004 | Axelson et al. | 623/20.21 |
| 2004/0186582 A1 * | 9/2004 | Yasuda et al. | 623/20.21 |
| 2004/0243244 A1 * | 12/2004 | Otto et al. | 623/20.27 |
| 2005/0055102 A1 | 3/2005 | Tornier et al. | |
| 2005/0102032 A1 | 5/2005 | Beynnon et al. | |
| 2005/0209701 A1 * | 9/2005 | Suguro et al. | 623/20.27 |
| 2006/0142867 A1 | 6/2006 | Metzger et al. | |
| 2008/0161918 A1 * | 7/2008 | Fankhauser et al. | 623/14.12 |
| 2009/0043396 A1 | 2/2009 | Komistek | |

* cited by examiner

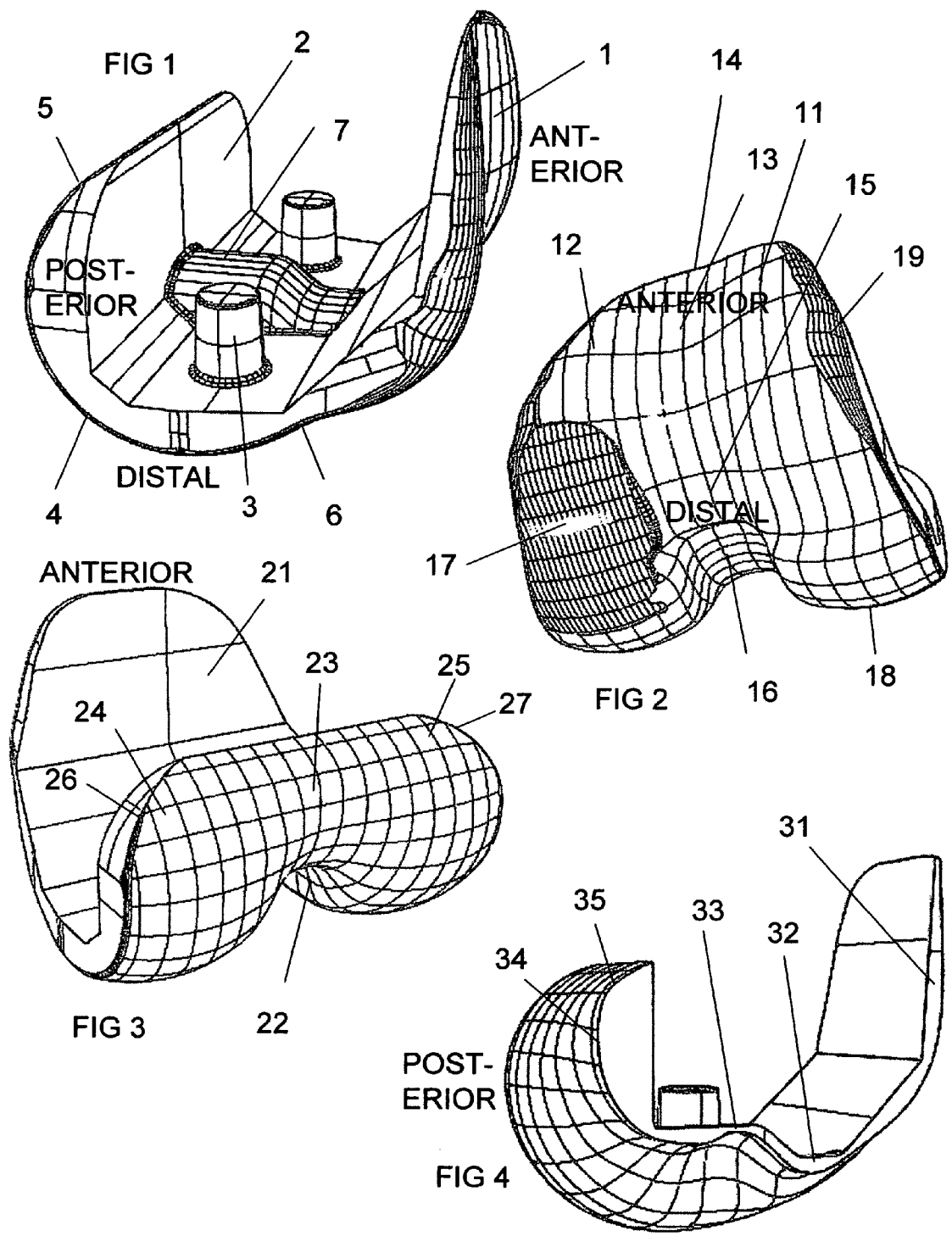

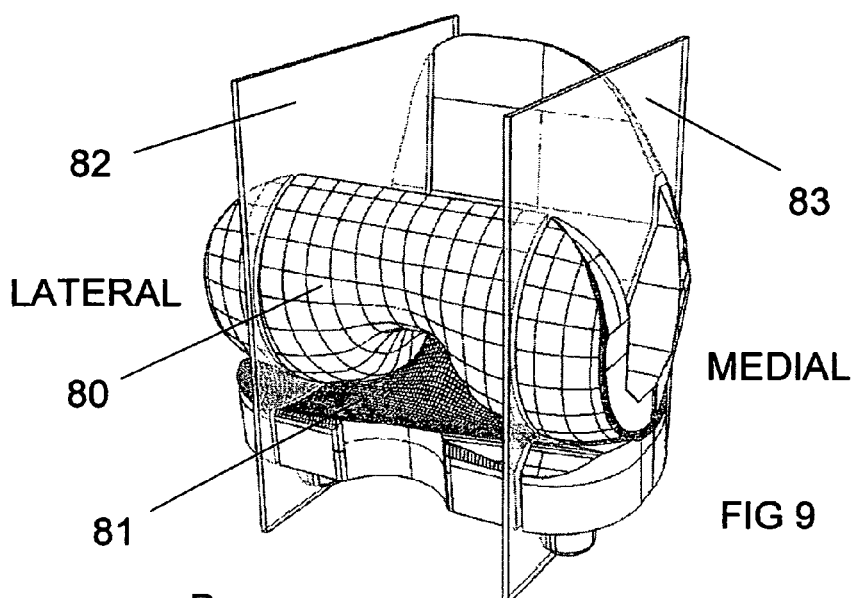
FIG 9
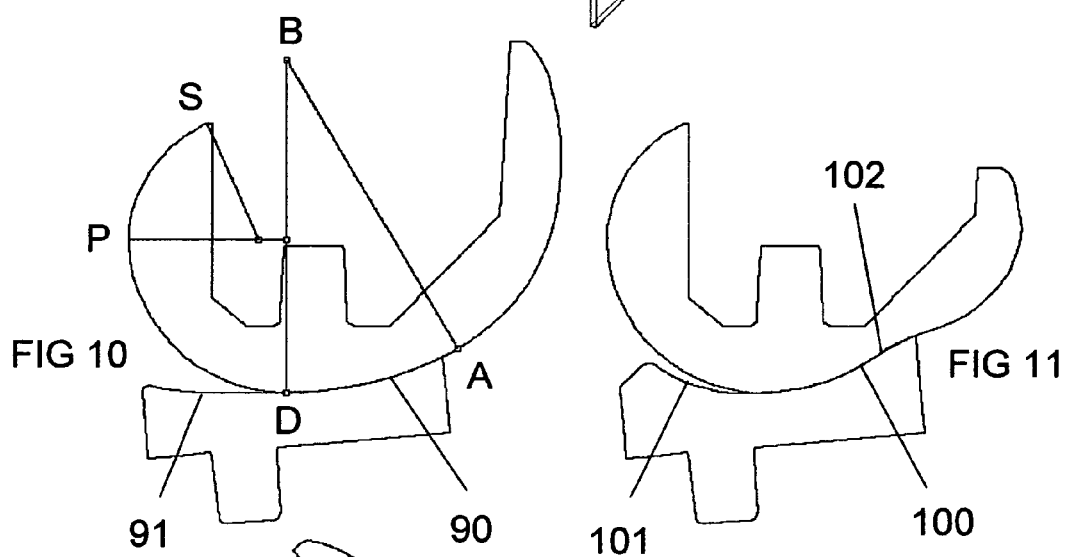
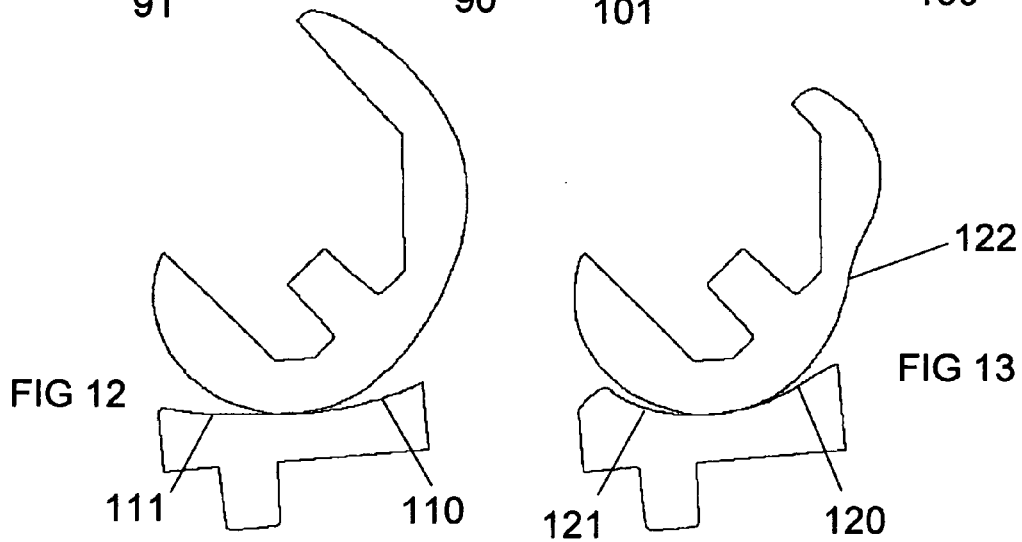

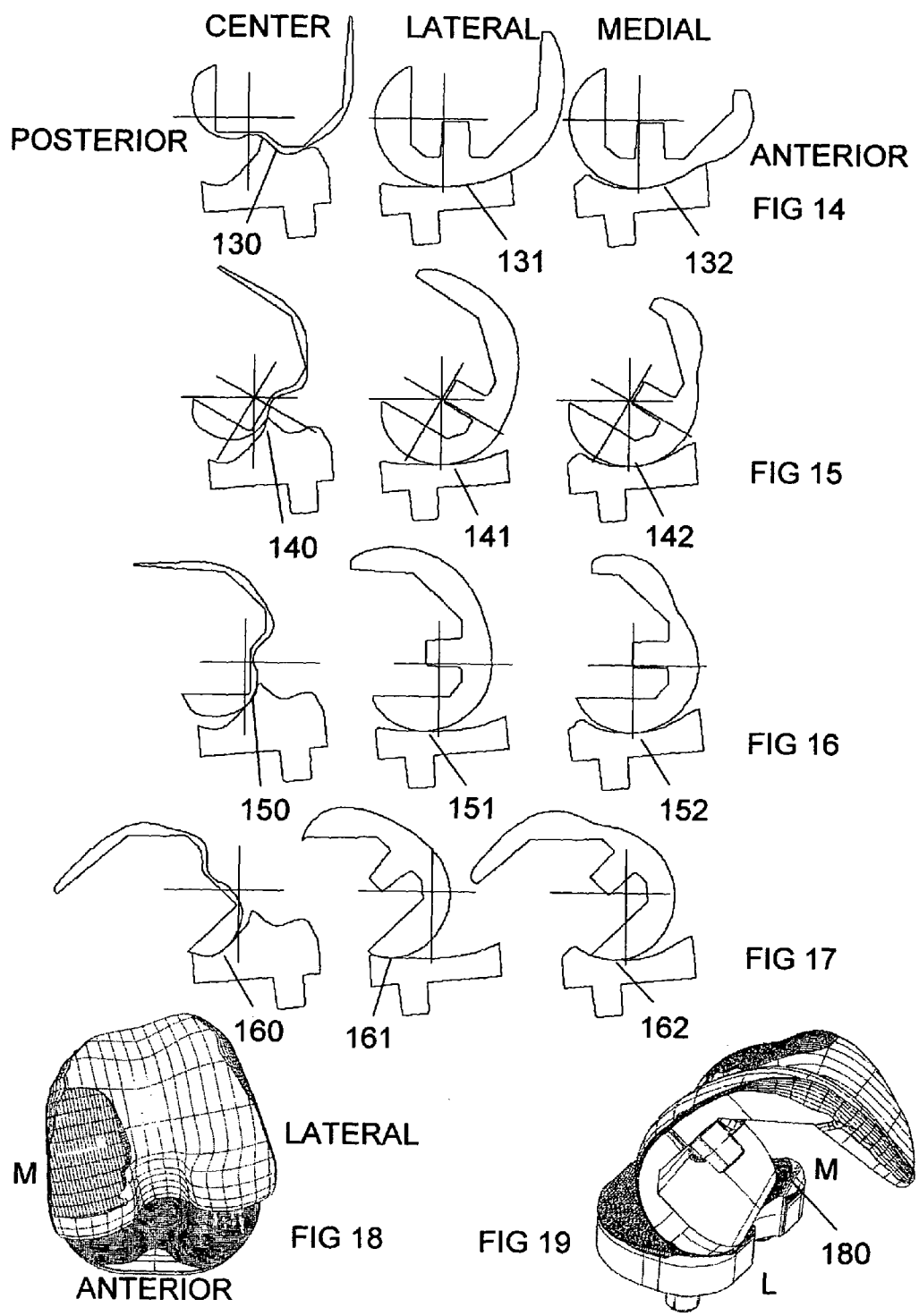

SURFACE GUIDED KNEE REPLACEMENT

CROSS-REFERENCE TO RELATED APPLICATIONS

This application is a continuation-in-part of co-pending U.S. patent application Ser. No. 11,304,107, filed Dec. 14,2005, hereby incorporated by reference.

FIELD OF THE INVENTION

The present invention relates to knee prostheses and more specifically to surface guided total knee replacement prostheses.

BACKGROUND

In an average person, the motion of the knee between the femur and the tibia is not unique. It varies with the person's muscle activity and the functions being performed.

Numerous studies have been performed on both the living knee and cadaveric specimens which determined general characteristics of knee motion, including a neutral path, and deviations about the neutral path which occur when shear forces or torques are superimposed.

Reference data for the normal knee has been obtained using fluoroscopy (Dennis, Komistek et al, 2001), as well as in a variety of other ways on both the living knee and in cadavers. It is now known that during flexion, the medial femoral condyle remains at an almost constant position on the tibial surface, whereas the lateral femoral condyle is displaced posteriorly, off the very back of the tibia in extreme flexion (Iwaki, Pinskerova et al, 2000; Nakagawa, Kadoya et al, 2000).

This movement pattern has been described as a synchronous flexion of the femur about an epicondylar axis and an internal tibial rotation about a vertical axis passing through the medial side of the tibia (Hollister, Jatana et al, 1993; Churchill, Incavo et al, 1998). Variations in the magnitude of the lateral displacement and the tibial rotation have occurred depending on the initial position of the feet on the ground and the activity performed, accommodated by the laxity of the knee (Hill, Vedi et al, 2000).

A relatively stable medial side has been a common factor in the above studies, except for a few millimeters of rollback and even upward levering in extreme flexion due to entrapment of the medial meniscus and impingement of the thigh on the calf. (Li et al, 2003; Conditt et al, 2006; Dawson et al, 2005; Yao et al, 2006; Most et al, 2005).

This normal motion has usually been disrupted however after Total Knee Replacement (TKR), as determined from fluoroscopy studies (Dennis, Komistek et al, 2003). In a deep knee bend, as the knee has flexed, there has been an anterior, rather than posterior, displacement of the femur on the tibia termed 'paradoxical motion'. The magnitude of internal rotation has been much less than normal on average. The effective pivot location has been variable, ranging from the medial side, the center, and the lateral side.

A striking finding has been the highly variable results from patient to patient. These findings are likely to be due to variations in the preoperative condition of the knees including muscles and soft tissues, to the resection of one or both cruciate ligaments, to the surgical placement of the components, and to the design of the TKR itself. In studies using other techniques, during various flexion-extension activities, the angle of the patella ligament to the long axis of the tibia was found to change from positive to negative during flexion in normal knees but remained almost constant after PCL retaining or substituting TKR (Pandit, Ward et al, 2005).

In studies where the neutral paths of motion were compared in specimens before and after TKR using a robot tester, a reduction of internal tibial rotation and posterior displacement after TKR compared with normal were common findings (Most, Li et al, 2005).

An additional factor is that the A-P stability of the medial side of the normal knee has not been present in a total knee (Blaha 2004). The kinematic abnormalities may reduce the maximum flexion angle achieved, reduce the efficiency of the quadriceps, alter patella mechanics, and not give the 'feeling of a normal knee' (Pritchett 2004).

While total knee replacement has been clinically successful, further functional improvements could possibly be made if the kinematics after a TKR more closely matched the intact state. Hence one possible design criterion relating to kinematics is that 'the neutral path of motion, and the laxity characteristics about that neutral path, is the same for an intact knee specimen, and after implantation of the total knee.'

In theory, this would result in knee kinematics in the living knee with the total knee implanted, the same as that of the knee in its normal intact state. In this context, laxity is defined by the shear force versus displacement, and torque versus rotation curves at a full range of flexion angles. This criterion has the limitation that an off-the-shelf total knee needs to be based on 'average' geometry and kinematics, and hence there may not be an exact match for any particular knee.

SUMMARY OF THE INVENTION

It describes in detail a particular artificial knee joint that has particularly favorable characteristics. The purpose of this embodiment is to replicate the characteristics of normal knee motion, both the neutral path and the laxity about the neutral path.

If a total knee is designed for resection of both of the cruciate ligaments, the criterion can be simplified to the requirement that 'the neutral path and the laxity of the total knee itself are the same as that of an average knee specimen.' That is the criterion -applied to the embodiment described here.

The major design features embodied are (1) the anterior medial recess on the femoral component interfacing with a pad on the anterior of the tibial surface, (2) relatively conforming medial bearing surfaces, (3) low conformity lateral bearing surfaces, and (4) a central post projecting from the center of the tibia, articulating inside a cupola in the center of the femoral component.

The combination of the above features provide progressive posterior displacement of the lateral femoral condyle from about sixty degrees flexion to maximum flexion, only a small posterior displacement of the medial femoral condyle, but some rotational laxity about the neutral position at all angles of flexion.

BRIEF DESCRIPTION OF THE DRAWINGS

Preferred embodiments of the invention are described below with reference to the drawings, wherein like numerals are used to refer to the same or similar elements.

FIG. 1 shows a side view of the femoral component with the anterior to the right and posterior to the left;

FIG. 2 shows an anterior and distal view of the femoral component;

FIG. 3 shows a posterior view of the femoral component;

FIG. 4 shows a side view of the femoral component where the medial half of the component has been removed;

FIG. 9 shows a postero-medial view of the femoral and tibial components with cutting planes through the central sections of the bearing surfaces;

FIG. 10 shows the femoral and tibial components through the lateral side at zero degrees flexion;

FIG. 11 shows the femoral and tibial components through the medial side at zero degrees flexion;

FIG. 12. shows the femoral and tibial components through the lateral side at forty-five degrees flexion;

FIG. 13. shows the femoral and tibial components through the medial side at forty-five degrees of flexion;

FIGS. 14, 15, 16, 17 show sagittal sections through the center of the component to show the tibial post and femoral cupola, through the lateral bearing surfaces and through the medial bearing surfaces;

FIG. 18. shows a top view of the femoral and tibial components at one hundred and thirty five degrees flexion; and FIG. 19 shows a perspective view of the femoral and tibial components during rotation from the lateral side at one hundred and thirty five degrees flexion showing the posterior displacement on the lateral side.

DETAILED DESCRIPTION OF THE PREFERRED EMBODIMENTS

Femoral Component (FIGS. 1 thru 4)

Figure 5:
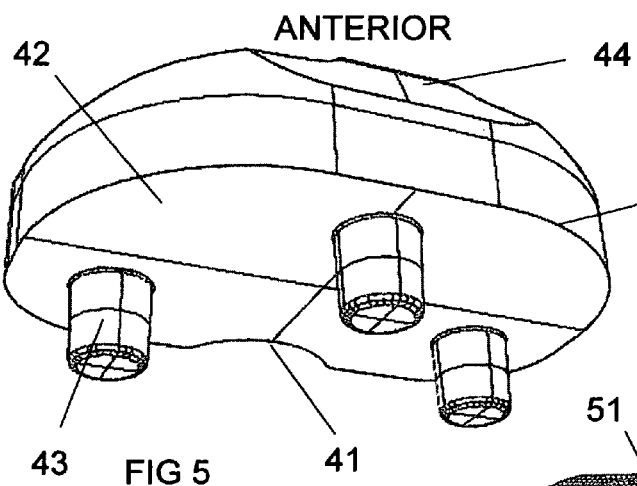
FIG. 5 shows a lower and anterior view of the tibial component.

FIG. 1 shows a side view of the femoral component with an anterior portion to the right and posterior portion to the left. The general shape of the femoral component resembles that of designs which are in common use in orthopedics. The shape is designed to replace the bearing surfaces of the distal femur and to fix rigidly on to the bone.

A patella flange 1 is at the anterior portion of the femoral component. The interior surface of the component 2 has five facets, which fit against the prepared surface of the bone which is cut likewise. Fixation to the bone can be by cement or by a bone ingrowth surface. In either case, augmentation of fixation can be provided by fixation pegs 3.

The bearing surface 4 which articulates with the tibia runs from the distal portion of the femoral component to the posterior portion. For contact in high flexion, the bearing surface 5 preferably has a reduced radius of curvature to facilitate high flexion.

At a distal-anterior location of the medial femoral condyle, there is a recess 6 which is a continuation of the distal radius 4. Its function will be described later.

In the center of the component is a protrusion 7 which houses an intercondylar cupola. This protrusion is a low profile protrusion such that it is housed within the intercondylar recess of the distal femur, requiring none or a very small amount of bone removal. This is advantageous because preservation of as much bone as possible preserves strength and makes any future revision much easier.

FIG. 2 shows an anterior and distal view of the femoral component. The lateral side of the patella flange 11 is more prominent than the medial side 12 which resembles the anatomical shape of the knee and provides the most stability to the patella. The lateral side is also where the forces are more concentrated.

Running down the center of the patella flange is the central groove which curves a few millimeters towards the lateral side as it nears the superior edge 14. The profile of the flange is such that it matches the profile of the anatomic patella. This profile is preserved until the distal region of the component 15, which articulates in high flexion.

Just beyond this region is the cupola 16 which has smooth contours between it and the surrounding bearing surfaces.

The anterior recess on the medial condyle 17 is essentially a continuation of the distal surface 4 with the same radius or close to the same radius. However a continuation of the exact profile of the distal surface would result in a cutout. Hence the recess is first generated and then the boundaries are blended in with the surrounding femoral surface. In particular, the recess so blended does not infringe substantially on the medial surface of the patella flange avoiding any problems of tracking of the patella.

Seen from the anterior, the profile of the femoral condyles 18 has a radius similar to that in the anatomic knee. The lateral 19 and medial edges of the femoral component are rounded so that soft tissues including muscles and capsule flow smoothly around the component during flexion-extension.

FIG. 3 shows a posterior view of the femoral component. The anterior facet of the inner five-facetted surfaces is shown 21. The posterior part of the cupola can be seen 22. As the cupola reaches the posterior portion, its depth reduces until it reaches the very posterior and then is at zero depth. The surface of the femoral component becomes cylindrical 23 except for roundings at the lateral 24 and medial 25 sides which are continuations of the frontal radii 18. The superior edges of the posterior condyles 26 27 are rounded to match the anatomy of the femur.

FIG. 4 shows a section of the femoral component where the medial half of the component has been removed. The contour of the base of the femoral groove is shown 31. This contour progresses to the distal end of the femur 32. Thereafter the cupola is formed which can have a variable depth relative to the depth of the patella groove. A normal patella groove depth is seven-eight mm. The cupola can be of the same depth or up to approximately twelve mm.

As will be described later, the lower depth results in a ramp on the tibial surface, whereas the larger depth results in a post, which is what is shown in this embodiment. The depth of the cupola reduces to zero at the posterior of the component 34. Above that point, the surface becomes cylindrical 35 as described above 23.

Tibial Component (FIGS. 5 thru 8)

FIG. 5 shows a lower and anterior view of the tibial component. The lower periphery 40 of the component matches the anatomic shape of the upper tibia.

The posterior recess 41 resembles the anatomic region where the posterior cruciate attaches down the posterior side of the tibia. In the design presented here, the posterior cruciate is excised because all of the necessary stability is provided by the bearing surfaces.

The lower surface 42 is interfaced against the cut surface of the upper tibia. This cut is made at about five degrees posterior slope to match the naturally occurring slope of the anatomic knee. The surface can have different means for fixing to the bone, the most common being with cement. However, the surface can be coated with a porous material, with hydroxyapatite or other materials for bone attachment. The fixation is augmented by three fixation pegs 43 although different peg configurations can be used including one central peg, two pegs, or four pegs.

The anterior portion of the component is chamfered thereby allowing the quadriceps tendon to slide over it without interference during high flexion, given that the angle of the tendon can be about ten-fifteen degrees to the vertical.

Figure 6:
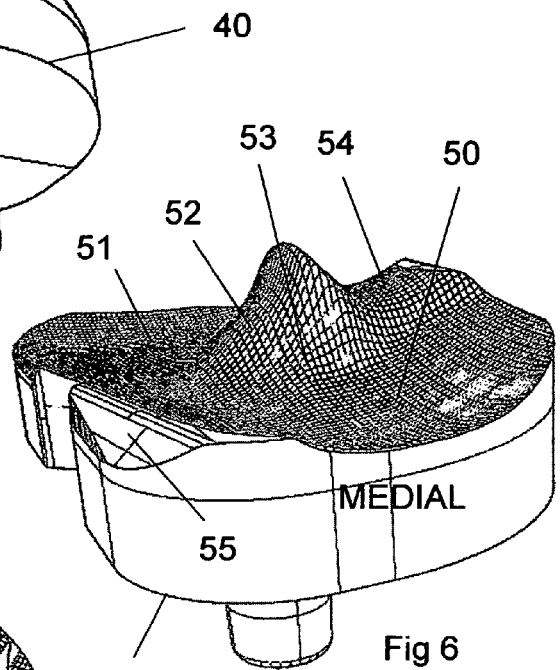
FIG. 6 shows a medial view of the tibial component.

FIG. 6 shows a medial view of the tibial component. This view shows the two sides of the bearing surface, the medial tibial bearing surface 50 and the lateral bearing surface 51.

A central post 52 is positioned in the center of the component in the medial-lateral direction and approximately central in the anterior-posterior direction. With the component at the five degrees posterior slope, the angle of the posterior side of the central post is approximately forty-five degrees, but can vary from this value. Ideally it should be steeper than forty degrees to avoid the femoral component from sliding up the post in extreme loading conditions.

On the other hand, the slope can be up to ninety degrees or even more. For our embodiment, however, the forty-five degree slope matches with the cupola shape and is considered close to optimal.

As shown, the medial side of the post 53 is radiused towards the medial side to allow for external rotation of the femoral component with flexion while maintaining a sufficient contact area. The anterior of the post 54 articulates with the anterior of the cupola at zero degrees flexion and in a few degrees of hyperextension. This provides good stability in extension and acts as a brake to hyperextension by making the contact anterior. It also provides a maximum lever arm for the posterior soft tissues that tense as full extension is reached.

The posterior part of the medial condyle 55 is chamfered to minimize impingement with the posterior medial femoral cortex in high flexion.

Figure 7:
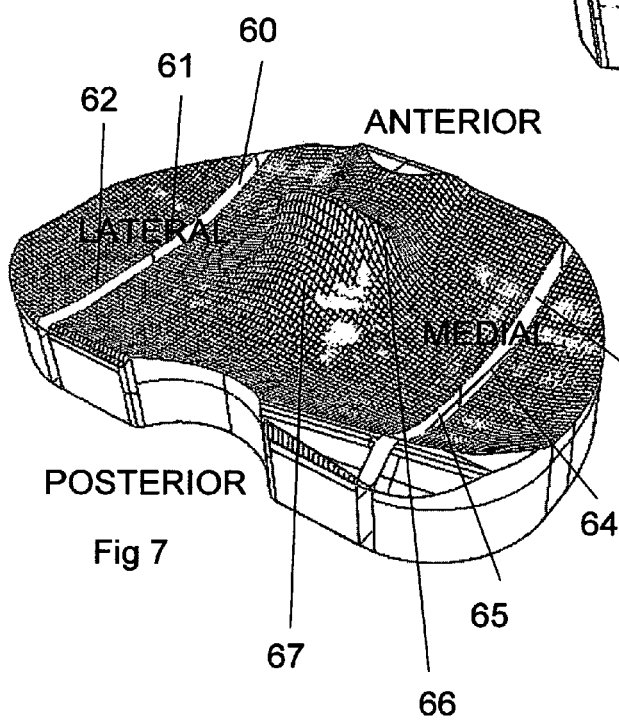
FIG. 7 shows a postero-medial view of the tibial component, where thin sagittal slices have been removed from the centers of the lateral and medial bearing surfaces to show more clearly the profiles of these surfaces in the sagittal view.

FIG. 7 shows a postero-medial view of the tibial component. Thin sagittal slices have been removed from the centers of the lateral and medial bearing surfaces to show more clearly the profiles of these surfaces in the sagittal view.

As shown, the anterior of the lateral surface 60 slopes upwards but is shallow and allows the femoral condyle to slide anteriorly several millimeters. The center of the lateral surface 61 is likewise shallow, as is the posterior surface 62. The latter allows for posterior sliding of the lateral femoral condyle.

The medial side has a different profile. In that, the anterior surface 63 slopes steeply upwards, almost matching the surface of the femoral condyle in the medial recess 6. These surfaces can be a perfect match but it is preferable to have a small clearance to avoid a rigid stop and to allow perhaps one millimeter of anterior motion before the motion is stopped by the steepness of the tibial surface. This part of the tibial surface is called an anterior pad because it was designed to fit the aforementioned recess in the femoral component.

Because the femoral recess is blended, the tibial surface surrounding the pad is likewise blended. The central part of the medial surface 64 is radiused to be slightly larger than that of the femoral surface 4. The posterior part of the tibial surface 65 is similarly radiused, and forms an upwards curve at the posterior of the tibia. The curve formed by 63, 64 and 65, allows for 2-3 mms maximum of posterior sliding of the femoral component, to avoid rigid positioning, to allow for some laxity, and to allow for some rollback which may be required in high flexion.

Figure 8:
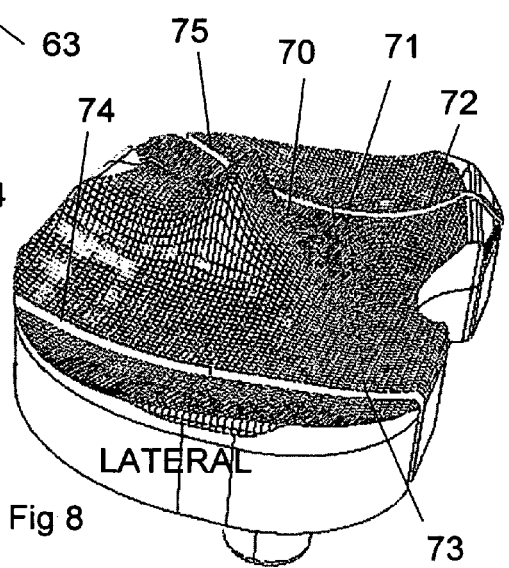
FIG. 8 shows a lateral view of the tibial component.

FIG. 8 shows a lateral view of the tibial component. As the femur is flexed beyond sixty degrees, the cupola contacts the post and the interaction causes a gradual posterior displacement of the femoral component on further flexion. However, this displacement takes place primarily on the lateral side of the bearing surface and not on the medial side. The reason is that the medial tibial surface is more dished than the lateral restricting posterior displacement of the medial side.

The lateral tibial surface is shallow, allowing the posterior displacement. Hence as flexion proceeds past sixty degrees there is progressive external rotation of the femoral component.

In order to avoid the cupola digging in to the corners of the post, the medial side of the post 70 is rounded. The medial femoral condyle remains at close to the lowest point on the tibial surface 71 because of the posterior upsweep of the surface 72.

On the other hand, the lateral femoral condyle steadily displaces posteriorly until it reaches point 73 in high flexion. The dotted line 71-73 shows the rotational position of the femoral component in high flexion. However, at each flexion position, there is some rotational freedom of the femoral component, just as in the anatomic knee.

Also shown on this figure is the shallow anterior upsweep on the lateral side 74 and the steeper upsweep on the medial side 75.

Anterior-Posterior Laxity and Stability

The purpose of the total knee design is to replicate the characteristics of normal knee motion, both the neutral path and the laxity about the neutral path.

FIG. 9 shows a postero-medial view of the replacement knee joint, with cutting planes through the central sections of the bearing surfaces. The femoral component 80 is positioned on the tibial component 81 at zero degrees flexion. The lowest points on the bearing surfaces are spaced at twenty-four millimeters on either side of the center giving a bearing spacing of forty-eight millimeters, but the bearing spacing can be varied from approximately forty to fifty millimeters. The lateral cutting plane 82 and the medial cutting plane 83 are at the above mentioned spacing.

FIG. 10 shows a section through the lateral side at zero degrees flexion. The radii of the bearing surfaces of the femoral component can be appreciated from this figure. The radius from D to P is slightly larger than from P to S, resembling the anatomic. The radius from D to A is approximately twice that from D to P, although this ratio can vary. In the anterior region 90, the femoral and tibial radii are in conformity or almost conforming with the difference in radii being approximately 0-2 mm. This will allow for only a small amount of anterior displacement. In the posterior region 91, there is a large difference in radii between the femoral and tibial surfaces, and posterior displacement is allowed.

FIG. 11 shows a section through the medial side at zero degrees flexion. In the anterior region 100, the femoral and tibial radii are in conformity or almost conforming, with the difference in radii being approximately 0-2 mm. This will allow for only a small amount of anterior displacement. In the posterior region 101, there is a small difference in radii between the femoral and tibial surfaces, and a small amount posterior displacement up to approximately two mm is allowed. Hence there is only a limited amount of anterior posterior laxity allowed on the medial side.

FIG. 12 shows a section through the lateral side at forty-five degrees flexion. In both the anterior 110 and posterior 111 regions, there is low conformity between the femoral and tibial surfaces allowing anterior-posterior laxity to occur.

FIG. 13 shows a section through the medial side at forty-five degrees of flexion. In both the anterior 120 and posterior 121 regions there is high conformity between the femoral and tibial surfaces allowing only about two to three millimeters of anterior-posterior laxity. The anterior recess on the femoral component 122 can be seen as a continuation of the radius from P to D.

External Femoral Rotation with Flexion

FIGS. 14, 15, 16, 17 show sagittal sections through the center of the component to show the tibial post and femoral cupola, through the lateral bearing surfaces, and through the medial bearing surfaces.

FIG. 14 is with the knee at zero flexion. The anterior of the femoral component locates on the anterior platform of the tibia 130, acting like an anterior cruciate ligament in providing anterior and posterior stability, and acting as the pivot if the knee goes into a few degrees of hyperextension. The lateral surfaces 131 are in conformity anteriorly but are in low conformity posteriorly. The medial surfaces 132 are in conformity both anteriorly and posteriorly.

FIG. 15 is with the knee at sixty degrees flexion. The copola just touches the top of the tibial post 140. The lateral surfaces have low conformity anteriorly and posteriorly 141 allowing some freedom of motion, which would allow rotational freedom because the medial surfaces 142 are still in close conformity.

FIG. 16 is with the knee at ninety degrees flexion. The cupola contacts the upper third of the post 150. The lateral contact 151 has shifted posteriorly while the medial contact is still central 152, resulting in some five degrees of external femoral rotation.

FIG. 17 is with the knee at one hundred and thirty five degrees flexion. The cupola contacts the post in the lower third and this action has resulted in further posterior displacement of the lateral femoral surface 161, while the medial side has moved posteriorly only about two mms 162.

FIG. 18 is a top view of the replacement knee joint at one hundred and thirty five degrees flexion. Due to the action of the cupola on the post, the low conformity lateral surfaces and the high conformity medial surfaces, there has been twelve degrees external femoral rotation, although this value could range from approximately ten to twenty degrees.

In FIG. 19, the rotation is seen from the lateral side. The medial femoral condyle is still located some distance from the posterior of the medial tibial surface, while the lateral femoral condyle is at the very posterior of the tibial surface. The posterior of the medial tibial component has been chamfered 180 in order to minimize the possibility of impingement with the posterior medial femoral cortex (not shown) in high flexion.

In the preceding specification, the invention has been described with reference to specific exemplary embodiments thereof. It will be evident, however, that various modifications, combinations and changes may be made thereto without departing from the broader spirit and scope of the invention as set forth in the claims that follow. It is understood that the present invention can combine one or more novel features of the different embodiments. The specification and drawings are accordingly to be regarded in an illustrative manner rather than a restrictive sense.

What is claimed is:

1. An artificial knee joint comprising:
   a femoral component comprising an anterior portion, a posterior portion, a distal portion and an interior surface, said femoral component further comprising:
      a patella flange located on said anterior portion of said femoral component, wherein a surface of said patella flange matches a profile of an anatomic patella;
      a low profile protrusion located on said interior surface of said femoral component;
      an intercondylar cupola, housed within said low profile protrusion, defining an opening on surface of said distal portion between a medial condyle and a lateral condyle, said intercondylar cupola characterized by smooth contours between said intercondylar cupola and a surrounding femoral bearing surface, said femoral bearing surface comprising a medial condylar surface that is substantially conformal, in a sagittal plane, with an articulating medial tibial dished surface for all flexion angles and operatively configured to limit anterior-posterior displacement of said medial condyle and a lateral condylar surface that has low conformity, in a sagittal plane, with an articulating lateral tibial dished surface and is operatively configured to permit anterior-posterior displacement of said lateral condyle, for flexion angles greater than approximately 60 degrees, wherein said medial and lateral condylar surfaces are dissimilarly shaped with said medial condylar surface comprising an anterior medial recess formed as a continuation of a distal radius in a sagittal plane.

2. The artificial knee joint of claim 1 whereby as the cupola reaches the posterior, a depth of the cupola reduces until at the very posterior it reaches a minimum of zero depth when the surface of the femoral component becomes cylindrical except for roundings at the lateral and medial sides which are continuations of the frontal radii.

3. The artificial knee joint of claim 1 whereby the cupola can be of the same depth as the central groove or up to approximately twelve mm.

4. The artificial knee joint of claim 1, wherein boundaries of said anterior medial recess are blended with the surrounding femoral surface.

5. An artificial knee joint, in accordance with claim 1, wherein said patella flange comprises a lateral side that is more prominent than medial side of said patella flange, and said patella flange further comprises a central groove that runs down a center of said patella flange, and curves toward the lateral side as it nears the superior edge of said femoral component.

6. An artificial knee joint comprising:
   a tibial component comprising:
      a medial dished surface that is substantially conformal with an articulating medial femoral condylar bearing surface, for all flexion angles, wherein anterior of said medial dished surface slopes upwards to form a pad, said pad having a surface conformal to a corresponding anterior medial recess in the surface of a medial femoral condyle, said medial dished surface defining a medial sagittal radius;
      a lateral dished surface that has low conformity with an articulating lateral femoral condylar bearing surface, wherein anterior of said lateral dished surface slopes upwards at a lesser slope than said medial dished surface, and a posterior of said lateral dished surface which slopes upwards, said lateral dished surface dissimilarly shaped with respect to said medial dished surface and defining a lateral sagittal radius that is larger than said medial sagittal radius;
      a vertically projecting central post positioned approximately in a center of the tibial component in both a medial-lateral direction and an anterior-posterior direction, said vertically projecting center post comprising a contact surface that is radiused towards the medial side and is operatively configured to contact a femoral intercondylar cupola at flexion angles greater than approximately 60 degrees and, in response to said contact, generate a force on said cupola in the posterior direction.

7. An artificial knee joint comprising:
a femoral component, the femoral component including an anterior portion, a posterior portion, a distal portion and an interior surface, the femoral component further comprising:
  a patella flange located on said anterior portion of said femoral component, wherein a surface of said patella flange matches a profile of an anatomic patella;
  a low profile protrusion located on said interior surface of said femoral component;
  an intercondylar cupola, housed within said low profile protrusion, defining an opening on surface of said distal portion between a medial condyle and a lateral condyle, said intercondylar cupola characterized by smooth contours between said intercondylar cupola and a surrounding femoral bearing surface, said femoral bearing surface comprising a medial condylar surface that is substantially conformal, in a sagittal plane, with an articulating medial tibial dished surface for all flexion angles and operatively configured to limit anterior-posterior displacement of said medial condyle and a lateral condylar surface that has low conformity, in a sagittal plane, with an articulating lateral tibial dished surface and is operatively configured to permit anterior-posterior displacement of said lateral condyle, for flexion angles greater than approximately 60 degrees, wherein said medial and lateral condylar surfaces are dissimilarly shaped with said medial condylar surface comprising an anterior medial recess formed as a continuation of a distal radius in a sagittal plane; and
a tibial component comprising:
  a medial dished surface that is substantially conformal with said articulating medial femoral condylar bearing surface, for all flexion angles, wherein anterior of said medial dished surface slopes upwards in the form of a pad, said pad having a surface conformal to said anterior medial recess in the surface of said medial femoral condyle, said medial dished surface defining a medial sagittal radius;
  a lateral dished surface that has low conformity with said lateral femoral condylar bearing surface, wherein anterior of said lateral dished surface slopes upwards at a lesser slope than said medial dished surface, and a posterior of said lateral dished surface which slopes upwards, said lateral dished surface dissimilarly shaped with respect to said medial dished surface and defining a lateral sagittal radius that is larger than said medial sagittal radius;
  a vertically projecting central post positioned approximately in a center of said tibial component in both a medial-lateral direction and an anterior-posterior direction, said vertically projecting center post comprising a contact surface that is radiused towards the medial side and is operatively configured to contact said femoral intercondylar cupola at flexion angles greater than approximately 60 degrees and, in response to said contact, generate a force on said intercondylar cupola in the posterior direction.

8. The artificial knee joint of claim 7 whereby the medial anterior pad of the tibial component slopes upwards closely matching the surface of said medial femoral condyle in the anterior medial recess.

9. The artificial knee joint of claim 7 whereby the central part of the medial tibial surface is radiused to be larger than that of the femoral surface in the sagittal plane.

10. The artificial knee joint of claim 7 wherein said anterior medial recess and said tibial pad are operatively configured to limit anterior displacement of the femur on the tibia thereby preventing paradoxical motion.

11. The artificial knee joint of claim 7 whereby the said tibial post and said cupola are operatively configured to cause a posterior translation of the femoral component on said tibial component with flexion, such displacement being more prominent on the lateral side compared with the medial side.

12. The artificial knee joint of claim 7, wherein boundaries of said anterior recess are blended with the surrounding femoral surface.

13. An artificial knee joint, in accordance with claim 7, wherein said patella flange comprises a lateral side that is more prominent than medial side of said patella flange, and said patella flange further comprises a central groove that runs down a center of said patella flange, and curves toward the lateral side as it nears the superior edge of said femoral component.

* * * * *